US00PP19851P2

(12) United States Plant Patent
Ludwig

(10) Patent No.: US PP19,851 P2
(45) Date of Patent: Mar. 24, 2009

(54) ***BRUNNERA* PLANT NAMED 'SILVER LINING'**

(50) Latin Name: *Brunnera macrophylla*
Varietal Denomination: Silver Lining

(75) Inventor: Kristin K. Ludwig, Aurora, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/001,144

(22) Filed: Dec. 10, 2007

(51) Int. Cl.
*A01H 5/00* (2006.01)

(52) U.S. Cl. ..... Plt./412

(58) Field of Classification Search ..... None
See application file for complete search history.

*Primary Examiner*—Kent L Bell
(74) *Attorney, Agent, or Firm*—Audrey Charles

(57) ABSTRACT

A new and distinct cultivar of *Brunnera* plant named 'Silver Lining', characterized by its medium blue-colored flowers, silver-coated medium green-colored foliage, and moderately vigorous, upright, clumping growth habit.

1 Drawing Sheet

Latin name of genus and species of plant claimed: *Brunnera macrophylla.*

Variety denomination: 'Silver Lining'.

BACKGROUND OF THE INVENTION

The present invention relates to a new and distinct cultivar of *Brunnera* plant botanically known as *Brunnera macrophylla* and hereinafter referred to by the cultivar name 'Silver Lining'.

The new cultivar originated in a controlled breeding program in Elburn, Ill. in the spring of 2003. The objective of the breeding program was the development of *Brunnera* cultivars having small-sized, silver-coated, medium green-colored foliage, with a compact growth habit.

The new *Brunnera* cultivar is the result of cross-pollination. The female (seed) parent of the new cultivar is the proprietary *Brunnera macrophylla* breeding selection designated PAS-A5516, not patented, characterized by its blue-colored flowers, medium green-colored foliage, and compact growth habit. The male (pollen) parent of the new cultivar is *Brunnera macrophylla* 'Jack Frost', U.S. Plant Pat. No. 13,859, characterized by its light blue-colored flowers, silver-coated, medium green-colored foliage, and a mounded, clumping growth habit. The new cultivar was discovered and selected as a single flowering plant within the progeny of the above stated cross-pollination during September 2003 in a controlled environment at Elburn, Ill.

Asexual reproduction of the new cultivar by division since September 2003 at Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Silver Lining' as a new and distinct cultivar of *Brunnera* plant:

1. Medium blue-colored flowers;
2. Silver-coated, medium green-colored foliage; and
3. Moderately vigorous, upright, clumping growth habit.

Plants of the new cultivar differ from plants of the female parent primarily in foliage color and from plants of the male parent primarily in flower color.

Of the many commercially available *Brunnera* cultivars, the most similar in comparison to the new cultivar is 'Alkanet', not patented. However, in side by side comparisons, plants of the new cultivar differ from plants of 'Alkanet' in the following characteristics:

1. Plants of the new cultivar have a leaf base different from plants of 'Alkanet';
2. Plants of the new cultivar have leaves with more green that borders the venation than plants of 'Alkanet'; and
3. Plants of the new cultivar have flower color that is darker than plants of 'Alkanet'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Silver Lining'. Measurements and numerical values represent averages of typical plants. The plants were grown in 6.5 inch pots for thirty weeks in a greenhouse at Elburn, Ill.

DETAILED BOTANICAL DESCRIPTION

Figure 1:
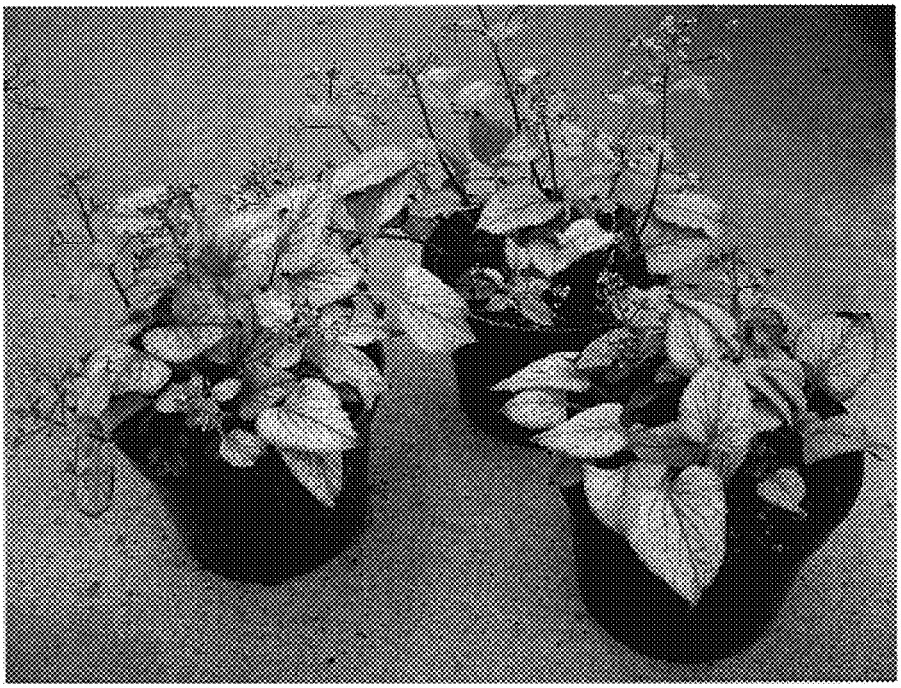
FIG. 1 illustrates a side view of the overall growth and flowering habit of 'Silver Lining'.
Figure 2:
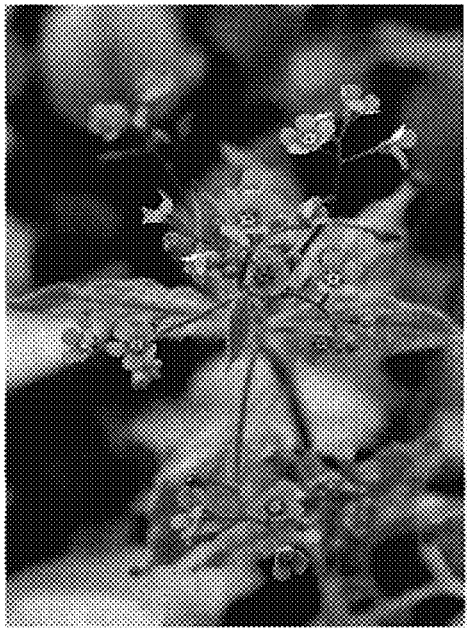
FIG. 2 illustrates a close-up view of an individual inflorescence of 'Silver Lining'.
Figure 3:
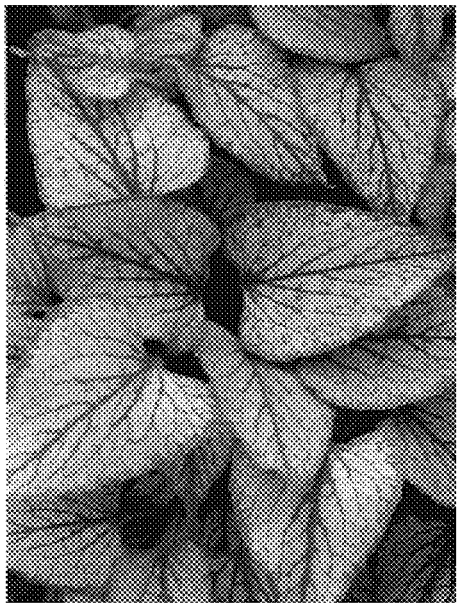
FIG. 3 illustrates a close-up view of the foliage of 'Silver Lining'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 13, 2007 between 9:00 a.m. and 11:00 a.m. under natural light conditions in West Chicago, Ill.

The following descriptions and measurements describe plants produced from cuttings taken from stock plants and grown in a poly-covered greenhouse under conditions comparable to those used in commercial practice. The plants were grown at Elburn, Ill. in 0.5 gallon pots for 7 months utilizing a soilless growth medium. Plants were initially established and grown with greenhouse temperatures approximately 70° F. to 77° F. (21° C. to 25° C.) during the day and approximately 65° F. to 68° F. (18° C. to 20° C.) during the night. The plants were dormant during winter months with an average greenhouse temperature of 50° F. (10° C.) during the day and an average of 40° F. (5° C.) during the night. Greenhouse light levels of 2,500 footcandles to 6,000 footcandles were maintained during the day.

Botanical classification: *Brunnera macrophylla* cultivar Silver Lining.

Parentage:

*Female parent.*—PAS-A5516, not patented.

*Male parent.*—*Brunnera macrophylla* 'Jack Frost' U.S. Plant Pat. No. 13,859.

Propagation:

*Type cutting.*—Division.

*Root description.*—Rhizomatous.

*Rooting habit.*—Freely branching.

Plant description:

*Commercial crop time.*—Approximately 15 to 22 weeks from a liner to finish in a 0.5 gallon pot.

*Growth habit and general appearance.*—Moderately vigorous, upright, clumping.

*Size.*—Height from soil level to top of plant plane: Approximately 21.7 cm. Width: Approximately 32.7 cm.

*Branching habit.*—Basal branching rosette. Quantity of main clumps per plant: Approximately 8.

Foliage description:

*General description.*—Fragrance: None. Form: Simple.

*Basal leaves.*—Arrangement: Solitary arising from rhizome. Aspect: Acute angle to perpendicular to petiole. Shape: Deltoid. Margin: Entire, often with one or two slight undulations. Apex: Acute. Base: Truncate, occasionally cordate. Venation pattern: Pinnate with veins depressed on adaxial surface and protruding on abaxial surface. Length: Approximately 6.0 cm. Width: Approximately 4.7 cm. Texture of upper surface: Setose. Texture of lower surface: Setose on venation. Color of upper surface: Entire surface has a silver appearing overlay color of closest to 192D, margins of 138B, and venation border of 138A. Color of lower surface: 138B with venation of 145D.

*Basal leaf petiole.*—Length: Approximately 11.0 cm. Diameter: Approximately 2.0 mm. Texture: Setose with a mixture of glandular and nonglandular hairs. Gland color: Colorless, transparent. Color: 148B with an overlay of 187B.

*Cauline leaves.*—Arrangement: Alternate. Aspect: Acute angle to perpendicular to rachis. Shape: Ovate. Margin: Entire, often with one or two slight undulations. Apex: Acute. Base: Attenuate. Venation pattern: Pinnate with veins depressed on adaxial surface and protruding on abaxial surface. Length: Approximately 3.1 cm. Width: Approximately 1.7 cm. Texture of upper surface: Setose. Texture of lower surface: Setose on venation. Color of upper surface: Entire surface has a silver appearing overlay color of closest to 192D, margins of 138B, and venation border of 138A. Color of lower surface: 138B with venation of 145D.

*Cauline leaf petiole.*—Length: Approximately 6.5 cm. Diameter: Approximately 3.0 mm. Texture: Setose. Color: 138A.

Flowering description:

*Flowering habit.*—'Silver Lining' flowers for approximately 3 weeks in the spring in outdoor conditions.

*Lastingness of individual flower on the plant.*—Approximately 5 to 7 days.

Inflorescence description:

*General description.*—Type: Paniculate cyme, arising from rhizome. Aspect: Facing upward. Quantity per plant: Approximately 7. Fragrance: None. Length or height: Approximately 21.4 cm. Width: Approximately 7.8 cm. Quantity of fully open flowers per inflorescence: Approximately 13.

*Peduncle.*—Shape: Angular with two parallel channels. Strength: Strong. Length or height: Approximately 13.6 cm. Width: Approximately 3.0 mm. Texture: Setose. Color: 148B with an overlay of 187B.

*Rachis.*—Shape: Cylindrical. Strength: Strong. Length or height: Approximately 9.8 cm. Width: Approximately 7.5 cm. Texture: Setose. Color: 148B with a faint overlay of 187B.

*Secondary rachis.*—Shape: Cylindrical. Strength: Strong, flexible. Aspect: Acute angle to perpendicular to stem. Length: Approximately 5.5 cm. Diameter: Approximately 1.7 cm. Texture: Setose. Color: 144A.

Flower description:

*General description.*—Type: Solitary, actinomorphic.

*Bud.*—Rate of opening: Generally takes 3 to 5 days for bud to progress from first color to fully open flower.

*Bud just before opening.*—Shape: Globose. Diameter: Approximately 2.0 mm. Texture: Glabrous. Color: N155B with petal margins of N78A.

*Corolla.*—Shape: Rotate. Diameter: Approximately 7.0 cm. Depth: Approximately 3.0 mm.

*Petals.*—Quantity: 5, fused at base. Shape: Obovate. Appearance: Dull. Margin: Entire. Apex: Obtuse. Length: Approximately 3.0 mm. Width: Approximately 2.0 mm. Diameter of throat: Approximately 1.0 mm. Color of pouch like swellings at throat opening: N155A with small streaks of 77A. Texture of upper and lower surfaces: Glabrous. Color of upper surface when fully open: 100B. Color of lower surface when fully open: 100D.

*Calyx.*—Shape: Star. Diameter: Approximately 3.0 mm.

*Sepals.*—Quantity per flower: 5, fused at base. Shape: Lanceolate. Apex: Acute. Length: Approximately 3.0 mm. Width: Approximately 1.0 mm. Texture of upper surface: Glabrous. Texture of lower surface: Setose. Color of upper surface: 143B. Color of lower surface: 143B.

*Pedicel.*—Strength: Strong. Aspect: Acute angle to secondary rachis. Length: Approximately 4.0 mm. Diameter: Less than 1 mm. Texture: Setose. Color: 143B.

*Reproductive organs.*—Androecium: Stamen quantity: 5, adnate to corolla tube. Stamen length: Approximately 1.0 mm. Filament color: N155A with small streaks of 77A. Anther shape: Winged. Anther color: N186A. Pollen amount: Moderate. Pollen color: 155D. Gynoecium: Pistil quantity: 1 per flower. Pistil length: Approximately 1.0 mm. Stigma shape: Round, capitate. Stigma color: 145D. Style color: 145D. Ovary shape: 4 lobed, deeply divided. Ovary color: N144C.

Seed and fruit production: Neither seed nor fruit production has been observed.

Disease and pest resistance: Resistance to pathogens and pests common to *Brunnera* has not been observed.

What is claimed is:

1. A new and distinct cultivar of *Brunnera* plant named 'Silver Lining', substantially as herein shown and described.

* * * * *